United States Patent [19]

Hosaka et al.

[11] 4,336,109
[45] Jun. 22, 1982

[54] METHOD FOR THE RECOVERY OF ACETONE

[75] Inventors: Hirokazu Hosaka, Ibaraki; Kenji Tanimoto, Ichihara; Kunihiko Tanaka, Toyonaka; Toshiharu Morita, Yao; Katsuyuki Shiota, Toyonaka; Yuji Ueda, Izumi; Seiichi Kai, Daito, all of Japan

[73] Assignee: Sumitomo Chemical Company, Limited, Osaka, Japan

[21] Appl. No.: 151,530

[22] Filed: May 19, 1980

[30] Foreign Application Priority Data

May 25, 1979 [JP] Japan .................................. 54-65151

[51] Int. Cl.³ .......................... B01D 3/34; C07C 49/08
[52] U.S. Cl. ........................................ 203/34; 203/35; 203/37; 203/71; 568/411
[58] Field of Search .................................... 203/33–37, 203/71; 568/410, 411

[56] References Cited

U.S. PATENT DOCUMENTS

| | | | |
|---|---|---|---|
| 1,542,538 | 6/1925 | Willkie | 568/411 |
| 2,555,185 | 5/1951 | Cromeans | 203/37 |
| 2,614,072 | 10/1952 | Carlson et al. | 203/37 |
| 2,971,894 | 2/1961 | Kendall | 568/411 |
| 3,276,973 | 10/1966 | Burmaster et al. | 203/37 |
| 3,330,741 | 7/1967 | Theilig et al. | 203/37 |
| 3,531,376 | 9/1970 | Minoda et al. | 203/37 |
| 3,672,961 | 6/1972 | Nixon | 203/37 |

FOREIGN PATENT DOCUMENTS

52-15473  4/1977  Japan.

*Primary Examiner*—Wilbur L. Bascomb, Jr.
*Attorney, Agent, or Firm*—Stevens, Davis, Miller & Mosher

[57] ABSTRACT

Acetone having a markedly low content of aldehydes is recovered from an aqueous rectification residue brought about by rectification of crude acetone carried out after one crude acetone having been alkali-treated or while an alkali or an aqueous solution thereof being added to the crude acetone, by mixing the aqueous rectification residue with an alkali, neutralizing the mixture to a pH of 4 to 9, and then subjecting the resulting mixture to distillation to obtain acetone as a distillate.

5 Claims, 1 Drawing Figure

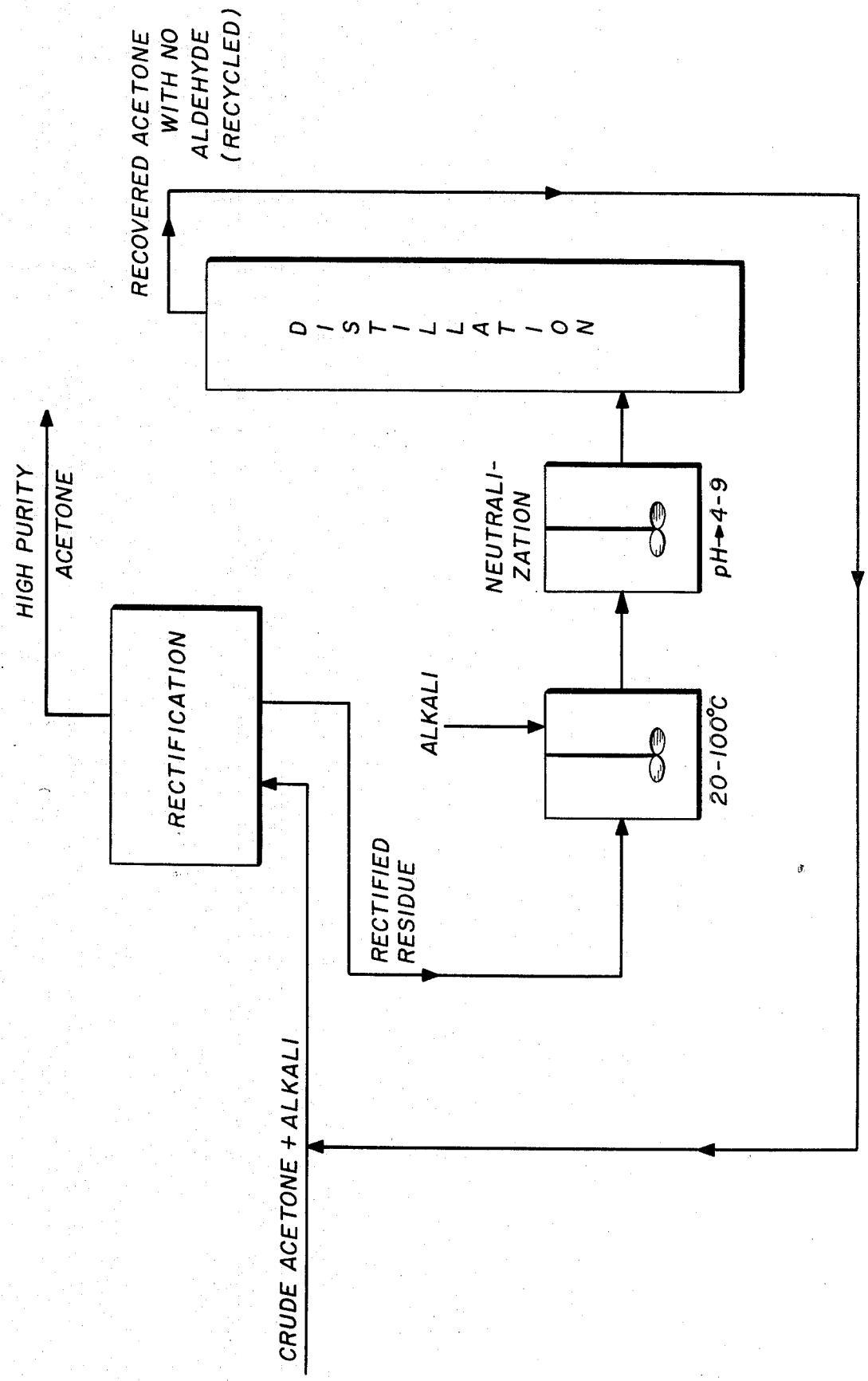

METHOD FOR THE RECOVERY OF ACETONE

The present invention relates to a method for the recovery of acetone from an aqueous distillation residue obtained after the purification of crude acetone.

Crude acetone produced by various methods or as a by-product generally contains various kinds of aldehydes including acetaldehyde. However, complete removal of these impurities by rectification alone, is difficult. As is well known, therefore, the crude acetone is first subjected to alkali treatment, that is, it is brought into contact with an alkali or aqueous alkali solution, followed by removal or neutralization of the alkali if necessary, and then rectification, or the crude acetone is subjected to rectification while adding an alkali or aqueous alkali solution. By these treatments, acetone of a higher purity free from aldehydes can be obtained. In this rectification, there remains an aqueous solution in a still as a residue (this aqueous solution is hereinafter referred to as "rectification residue" for brevity), which is treated and discarded as waste water. Since, however, the rectification residue contains organic substances in high concentrations, the waste water treatment is not easy and requires substantial expense.

For this reason, a method for the recovery of acetone from the rectification residue was disclosed (Published Examined Japanese Patent Application No. 15473/1977). This method comprises adding to the rectification residue an alkali to adjust the pH from 10 to 12, heating the mixture to convert high-boiling compounds contained in the rectification residue, for example, acetone condensates (e.g. diacetone alcohol) and acetone/aldehyde condensates to acetone, and then recovering the acetone by distillation.

Although the content of organic substances in the rectification residue can be decreased by this method, a problem is presented is that the recovered acetone is contaminated with a large quantity of aldehydes. Consequently, this method is not always said to be satisfactory.

For the reasons described above, the present inventors extensively studied a method for recovering high-purity acetone from the rectification residue without drawbacks as described above. As a result, it was found that acetone containing little aldehydes can be recovered by alkali-treatment of the rectification residue and then neutralization of the mixture to a pH of 4 to 9 prior to distillation. In addition, the waste water treatment of the resulting residue becomes very easy since the content of organic substances in the resulting residue is markedly decreased.

The present invention provides a method for the recovery of acetone from an aqueous rectification residue brought about by rectification of crude acetone carried out either after the crude acetone has been alkali-treated or while an alkali or while an aqueous alkali solution is being added to the crude acetone. The method comprises mixing the aqueous rectification residue with an alkali at a temperature of 20° to 100° C., neutralizing the mixture to a pH of 4 to 9, and then subjecting the resulting mixture to distillation to obtain acetone as a distillate.

The aqueous rectification residue to which the present invention is applied refers to a residual aqueous solution remaining in a still after acetone has been recovered from crude acetone by the abovementioned well-known method wherein the crude acetone is subjected to alkali-treatment, that is, it is brought into contact with an alkali or aqueous alkali solution, optionally followed by removal or neutralization of the alkali, and then rectification, or the crude acetone is subjected to rectification while adding an alkali or aqueous alkali solution. In this method, when the crude acetone contains no water, or, if any, a little water, aqueous alkali solutions are used as alkali. When the crude acetone contains water, alkali substances are added as they are or in aqueous solutions.

In accordance with the present invention, the aqueous rectification residue is subjected to alkali-treatment by mixing with an alkali. Examples of alkali metals, used in the present invention are sodium hydroxide, potassium hydroxide and aqueous solutions thereof. The amount of alkali is not particularly limited. It is however necessary that the pH of the mixture is 10 or more, particularly preferably 12 or more.

The alkali-treatment is carried out by stirring the mixture at a temperature ranging from room temperature (20° C.) to 100° C., and preferably at 40° to 70° C. After the alkali-treatment is finished, the mixture is neutralized with an acid. Any acid may be used for this purpose, but sulfuric acid, hydrochloric acid and phosphoric acid are preferably used. In this neutralization, the pH of the mixture is controlled to 4 to 9, preferably 5 to 8.

The recovery of acetone from the neutralized aqueous solution is carried out by distillation. The distillation may be a simple distillation, but rectification is particularly effective. This operation may be carried out batchwise or continuously in a manner well known to the persons skilled in this art.

Recovered acetone thus obtained may be used, as it is, for the desired purposes, or it may be further purified. Alternatively, it may be recycled to the crude acetone. Since the recovered acetone of the present invention is very low in aldehyde content as compared with that of the prior art, aldehydes do not accumulate in the treatment system unlike the prior art even though the recovered acetone is recycled to the crude acetone, and this makes the subsequent treatment very easy. Further, the resulting residue separated from the distillation in accordance with the present invention has a markedly decreased content of organic substances, and therefore the waste water treatment thereof becomes very easy. This is another superior effect of the present invention.

The accompanying single sheet of drawing is a schematic flow diagram illustrating the several steps of the process of this invention.

The present invention will further be illustrated with reference to the following examples, and it is to be understood that the invention is not limited thereto within the scope and spirit of the invention.

All parts in the examples are by weight.

EXAMPLE 1

Crude acetone (acetone content, about 95% by weight; water content, about 5% by weight) containing lower aliphatic aldehydes of 400 ppm based on the weight of acetone was brought into contact, at 50° C. for about 10 minutes, with an aqueous sodium hydroxide solution (sodium hydroxide concentration, about 0.5%) of 20% by weight based on the weight of the crude acetone. The mixed solution was allowed to stand, and a small amount of alkali liquor separated therefrom was removed, followed by neutralization with 0.3% aqueous sulfuric acid. By rectification of the acetone solution, purified acetone containing not more than 10 ppm of aldehydes was obtained as distillate, and an aqueous solution containing only about 1% of acetone was obtained as the rectification residue. The rectification residue contained about 25% of high-boiling organic substances.

To 100 parts of the rectification residue 0.5 parts were added of sodium hydroxide to adjust the pH to about 13, and the mixture was kept at 60° C. for about 1 hour with stirring. This aqueous solution was neutralized to a pH of 6 with sulfuric acid and then rectified to recover 24.2 parts of acetone (acetone content, 97% by weight; aldehyde content, 240 ppm based on acetone). The amount of this recovered acetone corresponds to 92% of acetone lost by deterioration in the foregoing rectification of the crude acetone.

COMPARATIVE EXAMPLE 1

One hundred parts of the rectification residue obtained in Example 1 was heat-treated with sodium hydroxide in the same manner as in Example 1, and then without neutralization with sulfuric acid, it was rectified, as it was, to recover 24.6 parts of acetone. The recovered acetone contained 97% by weight of acetone and aldehydes of 1200 ppm based on acetone. The amount of this recovered acetone corresponds to 93.5% of acetone lost by deterioration of the rectification of the crude acetone.

EXAMPLE 2

To 100 parts of the rectification residue obtained in Example 1 1 part of potassium hydroxide was added, and the mixture was kept at 50° C. for about 1 hour with stirring. This aqueous solution was neutralized to a pH of 7 with sulfuric acid and then rectified to recover 23.9 parts of acetone. The recovered acetone contained 97% by weight of acetone and aldehydes of 210 ppm based on acetone.

What is claimed is:

1. A method for the recovery of substantially aldehyde-free acetone from an aqueous rectification residue obtained as the bottoms product after rectification of crude acetone, said crude acetone having been treated with an alkali or an aqueous alkali solution either before or during said rectification, which method comprises mixing said aqueous rectification residue with an alkali at a temperature of 20° to 100° C., neutralizing the mixture to a pH of 4 to 9 and then subjecting the resulting mixture to further distillation to obtain acetone as distillate.

2. The method according to claim 1, wherein the alkali is sodium hydroxide, potassium hydroxide or an aqueous solution thereof.

3. The method according to claim 1, wherein the alkali is used in an amount sufficient to adjust the pH of the mixture to 10 or more.

4. The method according to claim 1, wherein the mixing is carried out by heating the mixture at a temperature of 40° to 70° C.

5. The method according to claim 1, wherein the neutralizing is carried out by the addition of an acid selected from sulfuric acid, hydrochloric acid and phosphoric acid.

* * * * *